United States Patent
Benje (10) Patent No.: US 7,435,983 B2
(45) Date of Patent: Oct. 14, 2008

(54) DEVICE FOR INJECTING ELECTROMAGNETIC RADIATION INTO A REACTOR

(75) Inventor: Michael Benje, Darmstadt (DE)

(73) Assignee: Uhde GmbH (DE)

( * ) Notice: Subject to any disclaimer, the term of this patent is extended or adjusted under 35 U.S.C. 154(b) by 270 days.

(21) Appl. No.: 10/554,555

(22) PCT Filed: Mar. 1, 2004

(86) PCT No.: PCT/EP2004/002023

§ 371 (c)(1),
(2), (4) Date: Sep. 11, 2006

(87) PCT Pub. No.: WO2004/096431

PCT Pub. Date: Nov. 11, 2004

(65) Prior Publication Data

US 2007/0034795 A1    Feb. 15, 2007

(30) Foreign Application Priority Data

Apr. 30, 2003   (DE) ............................... 103 19 811

(51) Int. Cl.
*H01J 49/00*   (2006.01)
*B01D 59/44*   (2006.01)
*H01S 3/09*    (2006.01)
*C23C 16/00*   (2006.01)

(52) U.S. Cl. ............... 250/505.1; 250/507.1; 422/129; 156/345.5; 372/70

(58) Field of Classification Search ............. 250/505.1, 250/507, 1; 422/129; 156/345.5; 372/70
See application file for complete search history.

(56) References Cited

U.S. PATENT DOCUMENTS 3,051,639 A    8/1962   Anderson et al.

(Continued)

FOREIGN PATENT DOCUMENTS

DE    1 952 770    5/1971

(Continued)

OTHER PUBLICATIONS

Clark, J.B. et al., "Laser initiated free-radical reactions", Applications of Lasers to Industrial Chemistry 458:82-88 (1984).

(Continued)

*Primary Examiner*—Nikita Wells (57) ABSTRACT

Device for injecting electromagnetic radiation into a reactor and a reactor comprising this device A device for injecting electromagnetic radiation into a reactor for carrying out free-radical gas-phase reactions and a reactor comprising such a device are described.

This comprises the elements:
a) a compartment which is separated from the reaction space of the reactor and is
b) connected to the reaction space of the reactor via at least one opening,
c) at least one feed line for introducing a flushing gas into the compartment, and also
d) at least one source of electromagnetic radiation which is arranged so that
e) the electromagnetic radiation passes through the compartment and the reaction space of the reactor adjoining the compartment.

The device and reactor make an increase in the yield of free-radical chain reactions possible.

11 Claims, 4 Drawing Sheets

U.S. PATENT DOCUMENTS

| | | | |
|---|---|---|---|
| 3,860,595 A | | 1/1975 | Kurtz et al. |
| 3,969,204 A | | 7/1976 | Neimann et al. |
| 4,414,671 A | * | 11/1983 | Wells et al. .................. 372/73 |
| 4,417,964 A | | 11/1983 | Wolfrum et al. |
| 4,584,420 A | | 4/1986 | Wiedrich et al. |
| 4,590,318 A | | 5/1986 | Longhini |
| 4,595,579 A | | 6/1986 | Prudhon et al. |
| 4,798,914 A | | 1/1989 | Link et al. |
| 4,843,182 A | | 6/1989 | Simonetta et al. |
| 4,851,597 A | | 7/1989 | Felix et al. |
| 5,488,190 A | | 1/1996 | Le Blevec et al. |
| 5,507,920 A | | 4/1996 | Schwarzmaier et al. |
| 5,997,835 A | | 12/1999 | Hyldtoft et al. |
| 6,030,506 A | | 2/2000 | Bittenson et al. |
| 6,166,277 A | | 12/2000 | Seidelbach |
| 7,270,724 B2 | * | 9/2007 | Elliott et al. ............ 156/345.5 |
| 2005/0124835 A1 | | 6/2005 | Benje et al. |
| 2007/0166212 A1 | * | 7/2007 | Pawlak et al. ............... 422/224 |

FOREIGN PATENT DOCUMENTS

| | | |
|---|---|---|
| DE | 1 953 240 | 5/1971 |
| DE | 0 027 554 | 4/1981 |
| DE | 29 38 353 | 4/1981 |
| DE | 30 08 848 | 9/1981 |
| DE | 33 28 691 | 2/1985 |
| DE | 36 30 162 | 3/1987 |
| DE | 43 42 042 | 6/1995 |
| DE | 44 20 368 | 12/1995 |
| DE | 196 48 999 | 5/1998 |
| DE | 198 45 512 | 4/2000 |
| DE | 200 03 712 | 8/2000 |
| EP | 0 027 554 | 4/1981 |
| EP | 0 264 065 | 4/1988 |
| EP | 0 276 775 | 8/1988 |
| EP | 0 705 857 B1 | 4/1996 |
| EP | 1 013 630 | 6/2000 |
| GB | 1 225 210 | 3/1971 |
| GB | 1 384 407 | 2/1975 |
| RU | 2 021 451 | 10/1994 |
| WO | WO-96/35653 | 11/1996 |
| WO | WO-00/29359 | 5/2000 |
| WO | WO-03/093207 | 11/2003 |

OTHER PUBLICATIONS

Wollrum, J., "Darstellung von Vinylchlorid durch laserinduzierete Radikal-Kettenreaktionen", Umschau, Forschung und Entwicklung, Chemische Synthesen mit Laserlicht 16:480:483 (1984).

* cited by examiner

DEVICE FOR INJECTING ELECTROMAGNETIC RADIATION INTO A REACTOR

RELATED APPLICATIONS

This application is a national stage application (under 35 U.S.C. 371) of PCT/EP2004/002023 filed Mar. 1, 2004 which claims benefit to German application 103 19 811.3 filed Apr. 30, 2003.

The present invention relates to a device by means of which electromagnetic radiation can be injected into a reactor, in particular for the photolytic generation of free radicals, and also a reactor equipped with the latter for carrying out free-radical chain reactions in the gas phase.

In carrying out free-radical chain reactions, it is frequently desirable to have large amounts of initiating free radicals available in order to increase the conversion in a given reaction volume and under otherwise identical conditions.

Free-radical gas-phase reactions have been carried out industrially for many years. One of the measures for improving the economics of the processes could be to seek very high reaction conversions. For this purpose, promoters have been added to the feed gas. These are compounds which disintegrate into free radicals under the conditions prevailing in the reactor and enter into the chain reaction which leads to formation of the desired products. The use of such compounds is known, for example from U.S. Pat. No. 4,590,318 or DE-A-3,328691.

It has been proposed that halogen-containing aliphatic hydrocarbons be dissociated into free radicals with the aid of laser light and these be used in free-radical chain reactions, e.g. for the preparation of vinyl chloride. Examples may be found in SPIE, Vol. 458 Applications of Lasers to Industrial Chemistry (1984), pp. 82-88, in Umschau 1984, Number 16, p. 482, and in DE-A-2,938,353, DE-C-3,008,848 and EP-A-27,554. However, this technology has not been introduced into industrial production up to the present time. A reason may be that the reactors proposed hitherto are not suitable for long-term operation.

In carrying out free-radical gas-phase reactions, the formation of by-products is to be expected. These contaminate the reactor during long-term operation and are deposited in the reactor, for example as carbon deposits.

Particularly when using promoter substances, the carbon formation rate increases because the promoters have to be used in amounts which have an appreciable effect on the reaction system.

These disadvantages nullify the economic advantage gained by the increase in conversion and lead to the use of promoter substances not having become established in industrial practice to the present day.

The problems of carbon formation have been described in DE-A-30 08 848. There, the photochemical initiation of a free-radical chain reaction by direct radiation of light into the reaction space, using both metal vapor lamps and also lasers as light source, is proposed. The observation that the window rapidly becomes covered with by-products when continuously operating light sources such as metal vapor lamps are used while it remains free when lasers are used is also described there.

A remedy proposed is to operate using a high flow velocity in the region of the optical window so that the by-products formed are formed in appreciable amount only downstream of the window.

However, this procedure has the disadvantage that the "self-cleaning" of the window is probably restricted to the use of pulsed lasers since in this case pressure pulses are generated in and around the carbon particles by brief local heating of the gas and then knock the carbon particles or the carbon layer off the window. Although the use of pulsed lasers is not explicitly mentioned in DE-A-30 08 848, it is mentioned in DE-A-29 38 353 which is explicitly incorporated by reference into DE-A-30 08 848.

The experiments on which DE-A-30 08 848 and DE-A-29 38 353 are based were carried out in fused silica reactors. However, in the case of industrial reactors made of metal, carbon deposits are formed even in the inner region of the reactor and thus "upstream" of any optical window installed. Possible causes are firstly that carbon precursors are formed in the inlet region of the reactor and secondly that even when the starting materials are carefully purified by distillation, small amounts of carbon precursors are introduced into the reactor together with the starting materials in an industrial process. There is therefore a need for further processes which can be implemented in a simple manner in industrial practice and in which formation of carbon deposits can be effectively avoided.

The present invention circumvents these disadvantages and provides a device or a reactor in the case of which light can be injected into a reactor operated under the conditions of thermal dissociation of hydrocarbons. For this purpose, a flushing gas is fed into a compartment which is separate from the actual reaction space and through which radiation from the radiation source passes and this flushing gas is then introduced into the reaction space.

It is an object of the present invention to provide a device for injecting electromagnetic radiation into a reactor which can be used in long-term operation and in the case of which the tendency for carbon formation or the deposition of carbon on the optical windows or light conductors is significantly reduced compared to known devices.

A further object of the present invention is to provide a reactor which can in a simple fashion be joined in a gastight manner to a device for injecting electromagnetic radiation even under conditions of high temperatures.

Yet another object of the present invention is to provide a device and a reactor for carrying out free-radical chain reactions, in the case of which higher. conversions compared to conventional reactors can be achieved at the same operating temperature or a reduction in the operating temperature compared to conventional reactors is possible at identical conversions.

The present invention relates to a device for injecting electromagnetic radiation into a reactor for carrying out free-radical gas-phase reactions, which comprises the elements:

a) a compartment which is separated from the reaction space of the reactor and is b) connected to the reaction space of the reactor via at least one opening, c) at least one feed line for introducing a flushing gas into the compartment, and also d) at least one source of electromagnetic radiation which is arranged so that e) the electromagnetic radiation passes through the compartment and the reaction space of the reactor adjoining the compartment.

The device of the invention, is connected to a pipe for the flushing gas which opens into the compartment.

A flushing gas is introduced into the reactor via the device of the invention.

This flushing gas can be an inert gas and/or a gas comprising dissociation promoters and/or gases which represent constituents of the reaction system and/or gaseous reducing agents.

In the case of dissociation promoters, they are photolytically dissociated in the compartment immediately before introduction into the reactor or in the irradiated region downstream of the opening of the compartment into the reactor.

Examples of inert gases are gases which are inert under the reaction conditions prevailing in the reactor, e.g. nitrogen, noble gases, e.g. argon, or carbon dioxide.

Examples of gases which represent constituents of the reaction system are gases which comprise the components of the feed gas stream.

An example of a gaseous reducing agent is hydrogen.

Promoters for use in the photolytic decomposition in the device of the invention and for introduction into the reactor are known per se. They are compounds which disintegrate into active species such as free radicals under the action of radiation and promote the free-radical chain reaction in the reaction space of the reactor.

Typical temperatures of the gas stream in the interior of the reactor at the position of the device for injecting electromagnetic radiation are dependent on the type of gas-phase reaction and encompass a wide range, for example from 250 to 1300° C.

The effect brought about by the gas fed in via the device of the invention is dependent not only on the temperature selected but also on the nature of the radicals generated and on their amount. It is usual to introduce a total of not more than 10% by weight of flushing gas, preferably not more than 5% by weight, in particular from 0.0005 to 5% by weight, based on the total mass flow, into the reactor.

It is assumed that the introduction of flushing gas prevents the deposition of carbon on the parts which are located in the optical path.

In addition, free radicals are generated photolytically when promoters are used, which promotes the free-radical chain reaction in the reaction mixture since an increased concentration of free radicals is ultimately available.

Preference is given to at least one device according to the invention being located in the vicinity of the point at which the feed gas stream enters the reactor. As a result, a high concentration of free radicals is formed at the point at which the feed gas enters the reactor and these radicals contribute to an efficient chain reaction.

In a preferred variant of the reactor of the invention, the reaction mixture comes into contact with a plurality of devices according to the invention while passing through the reactor.

Very particular preference is given to the number of devices according to the invention in the first third of the reactor being greater than in the second third and/or in the third third.

The invention also provides a reactor for carrying out free-radical gas-phase reactions, into which at least one of the above-defined devices opens.

The reactor comprises at least the following elements:
i) a feed line for the feed gas stream opening into the reactor,
ii) at least one above-defined device comprising a compartment and opening into the reactor for injecting electromagnetic radiation into the reactor,
iii) a feed line for a flushing gas opening into the compartment of the device
iv) a source of a flushing gas connected to the feed line,
v) if appropriate, a heating device for heating the flushing gas in the feed line,
vi) a heating device for heating and/or maintaining the temperature of the gas stream in the reactor, and
vii) a discharge line for the product gas stream of the free-radical gas-phase reaction leading from the reactor.

As reactor, it is possible to use all types known to those skilled in the art for such reactions. Preference is given to a tube reactor.

The reactor of the invention can be followed by an adiabatic after-reactor which preferably comprises the above-defined elements ii), iii) and iv). In the adiabatic after-reactor, the heat of reaction required is supplied by the heat of the product gas stream introduced, which cools down as a result.

Instead of the combination of the reactor of the invention with an adiabatic after-reactor comprising the elements ii), iii) and iv), it is also possible for such an adiabatic after-reactor to be combined with a reactor known per se which does not have the elements ii), iii) and iv).

The device of the invention opens into the interior of the reactor of the invention and feeds a flushing gas into the feed gas stream as it passes through the reactor and allows injection of electromagnetic radiation into the interior of the reactor.

The flushing gas (mixture) flows through the compartment preceding the actual reaction space and then passes through an opening which can be configured as a nozzle, into the actual reaction space.

To carry out the photolysis, electromagnetic radiation from a radiation source suitable for the purposes described is injected through an optically transparent window, preferably a fused silica window, or via a light conductor into a compartment which is separate from the actual reaction space and passes through the compartment itself and also through part of the adjoining reaction space.

In the compartment, the flushing gas forms a gas cushion which largely separates the optical components e.g. the optical window, from the reaction space in chemical terms. The correctness of this measure will be illustrated below with the aid of an example.

An undesirable secondary reaction when carrying out free-radical gas-phase reactions is the deposition of carbon on the reactor walls. The process of carbon deposition proceeds more slowly on nonmetallic materials such as fused silica then on metallic materials. This fact is now utilized for slowing carbon formation in reactor tubes by applying nonmetallic coatings to the interior wall of the tube. Despite this fact, carbon would also be deposited on the optical components if these were exposed directly to the reaction mixture, i.e. installed directly in the reactor wall.

The present invention circumvents the disadvantages of previously known processes and provides a device and a reactor which enable electromagnetic radiation to be injected into a reactor operated under the conditions of the free-radical gas-phase reaction.

Particularly preferred embodiments of the device of the invention and their preferred arrangement in a reactor are described below with reference to the FIGS. 1, 2, 3 and 4.

Figure 1:
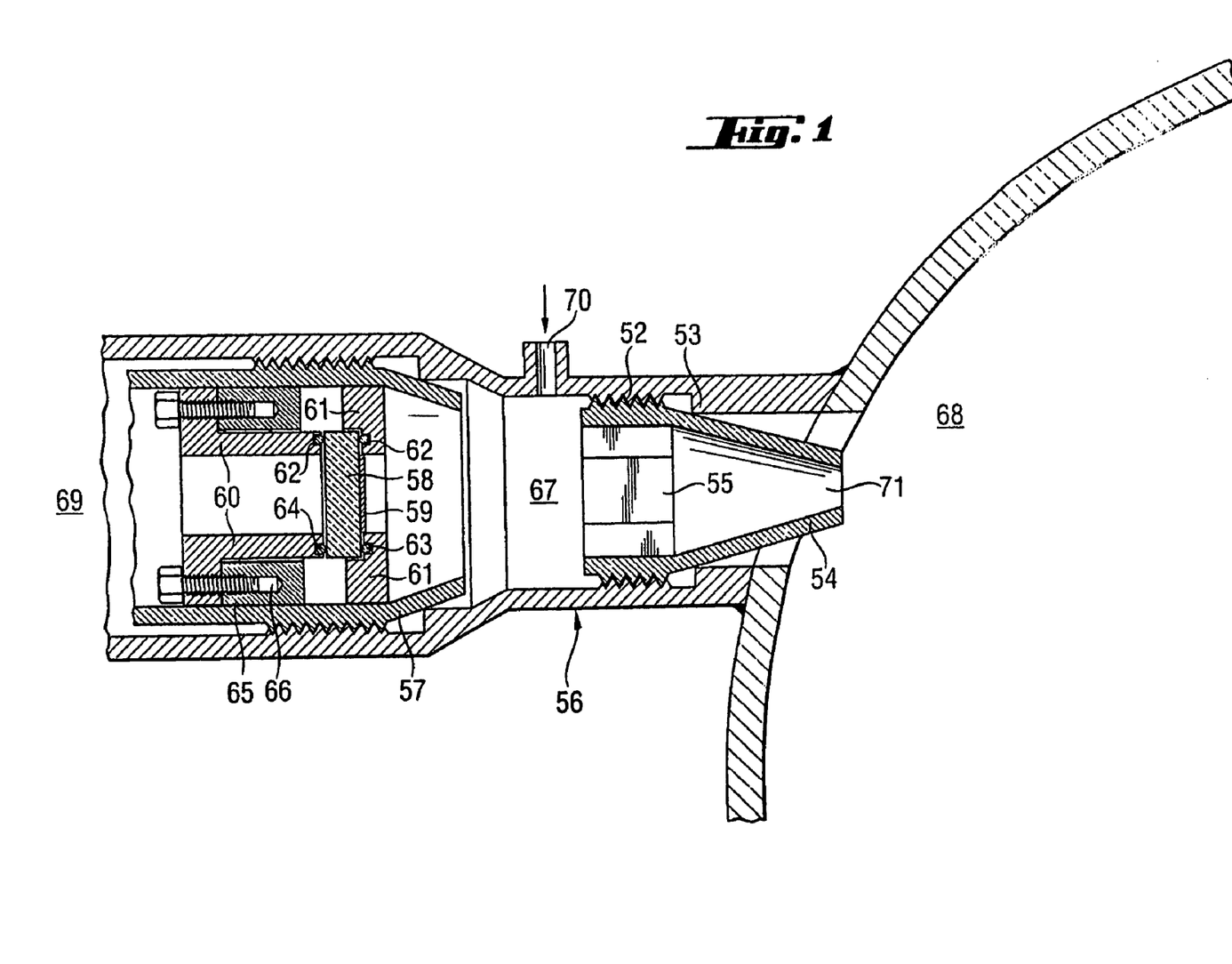
FIG. 1 shows a preferred device for generating free radicals from dissociation promoters by means of electromagnetic radiation and for introducing the flushing gas into a free-radical gas-phase reactor, depicted in longitudinal section.

In the figures:

FIG. 1 shows a device preferably used for injecting electromagnetic radiation and its installation in the reactor of the invention.

A holder which has a thread (52) and a circumferential sealing edge (53) in its interior is welded on at a bend of the reaction tube. A conical barrel (54) whose front end can be configured as a nozzle and which can, for example, have an internal hexagon (55) to make screwing easier can be screwed into this holder. When the conical barrel (54) is screwed into the holder (56), it forms, together with the sealing edge (53) of the holder, a seal which is reliable under the conditions of the reaction. This proven sealing principle has been described in DE-A-44 20 368. Likewise as described in DE-A-44 20 368, an additional seal can be produced by means of a stopping box packing (not shown in FIG. 1).

A further barrel (57) containing an optically transparent window (58), e.g. a fused silica window, which can be coated with an optically semitransparent metal layer (59), with the metal preferably being a hydrogenation catalyst and very particularly preferably being a platinum metal, can be screwed into the holder (56) using the same sealing principle.

The optical window is clamped between holders (60, 61) which on their sides facing the window have circumferential recesses (62) which accommodate a seal (63, 64) preferably a metal seal and very particularly preferably a gold seal.

The window (58) is pressed against the holder (61) by the holder (60). This can be achieved by screwing the holder (60) onto a bearing ring or bearing blocks (65) which is/are provided, for example, with holes (66) having a closed end.

The holders (60) and (61), the recesses (62) and the thicker seal are dimensioned so that when the assembly is screwed together a defined pressure of the seals is established and the optical window is not damaged.

The intermediate space (67) between the barrels (54) and (57) is provided with one or more gas feed lines and forms a compartment which is separated from the reaction space (68) and from the outside (69).

The free-radical gas-phase reaction takes place in the reaction space (68). The entire assembly is in the case of tube reactors preferably installed at a bend of the reaction tube which projects from the actual radiation zone of the furnace and is thermally insulated therefrom.

A flushing gas, e.g. nitrogen or a noble gas, or a mixture of an inert gas with a promoter substance or a gaseous promoter substance flows through the gas inlet (70) into the compartment (67). The gas leaves the compartment and flows through the opening (71) into the reaction space.

As a result of the permanent flushing of the compartment, the optical window is separated from the reaction space (68) by a gas cushion. Carbon precursors such as acetylene, benzene or chloroprene can therefore not reach the window and form carbon deposits there.

In a preferred embodiment, the optical window is coated with an optically semitransparent metal layer, with the metal being a hydrogenation catalyst, e.g. palladium.

If a small amount of hydrogen is then mixed into the promoter gas, carbon precursors which despite flushing reach the optical window are reduced at its surface. As a result, no carbon deposits can form on the surface of the window.

The radiation from the radiation source passes through the optical window and transfers energy to the molecules of the reaction mixture in the reaction space (68) and to any promoter substance present in the compartment (67). This generates free radicals (photolysis) which then promote the reaction occurring in the actual reaction space (68).

The generation of free radicals and their subsequent transport into the reaction space is normally difficult, since the free radicals rapidly recombine under the prevailing pressure conditions (typically 9-25 bar). However, in the case of the arrangement according to the invention, the radiation passes through the entire compartment and also the reaction space. This results in the desired free radicals also being formed in the opening (71) and in the zone of the reaction space adjoining this opening and thus reliably being able to participate in the reaction. It is therefore not necessary for the flushing gas to have a high flow velocity.

In a further embodiment, the outer wall of the device in particular the part of the device which projects into the reaction space, can be coated with an inert material, e.g. a metal oxide, ceramic, boron nitride or silicon nitride.

Figure 2:
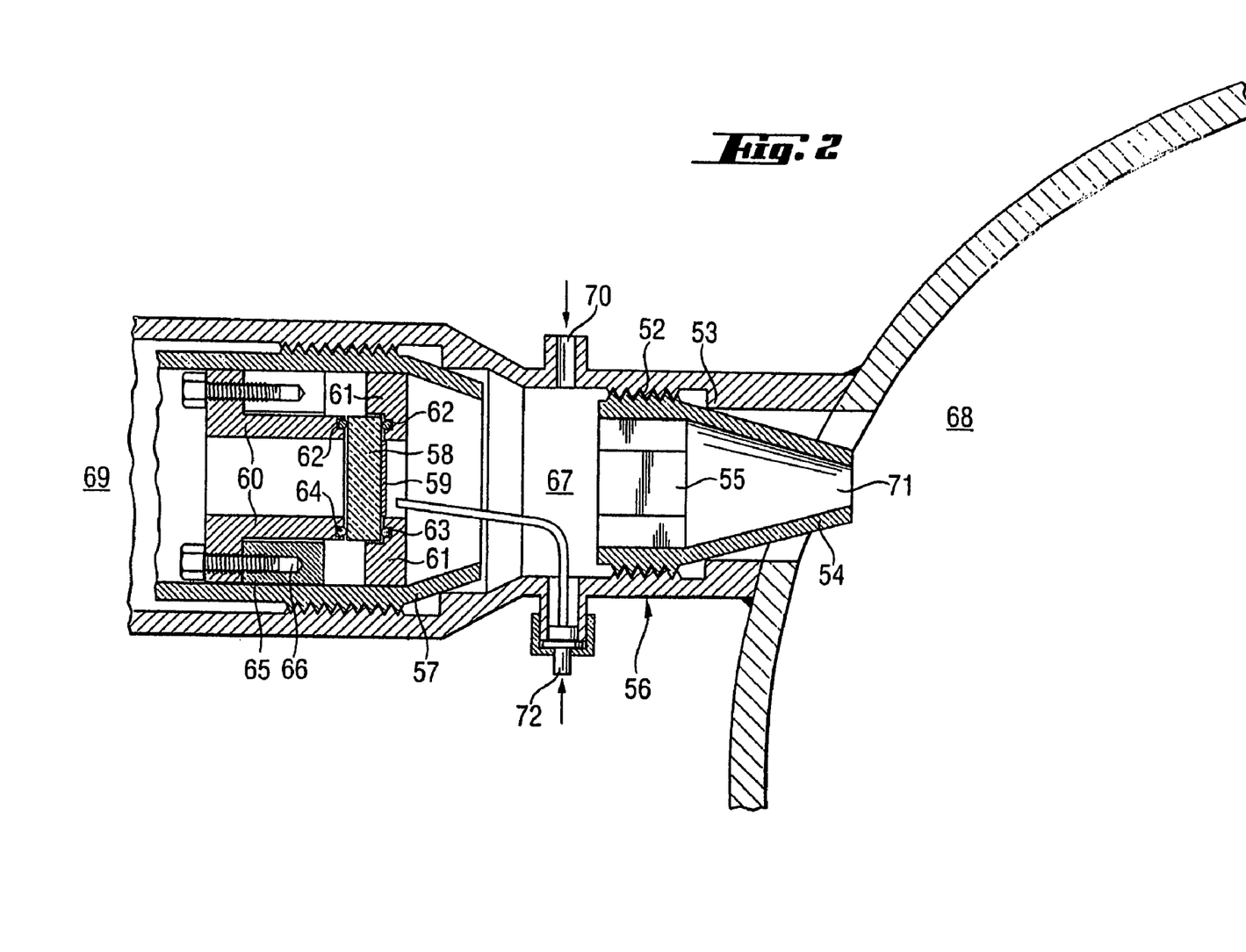
FIG. 2 shows a modification of the device of FIG. 1 depicted in longitudinal section.

In a further preferred embodiment as shown in FIG. 2, the compartment (67) has a further gas inlet (72) which continues to close to the surface of the optical window (58). This makes it possible to flush the window and its immediate environment with gas, while a further part of the flushing gas is introduced through the gas inlet (70). Such an arrangement allows the optical window to be protected even better against carbon deposits.

Figure 3:
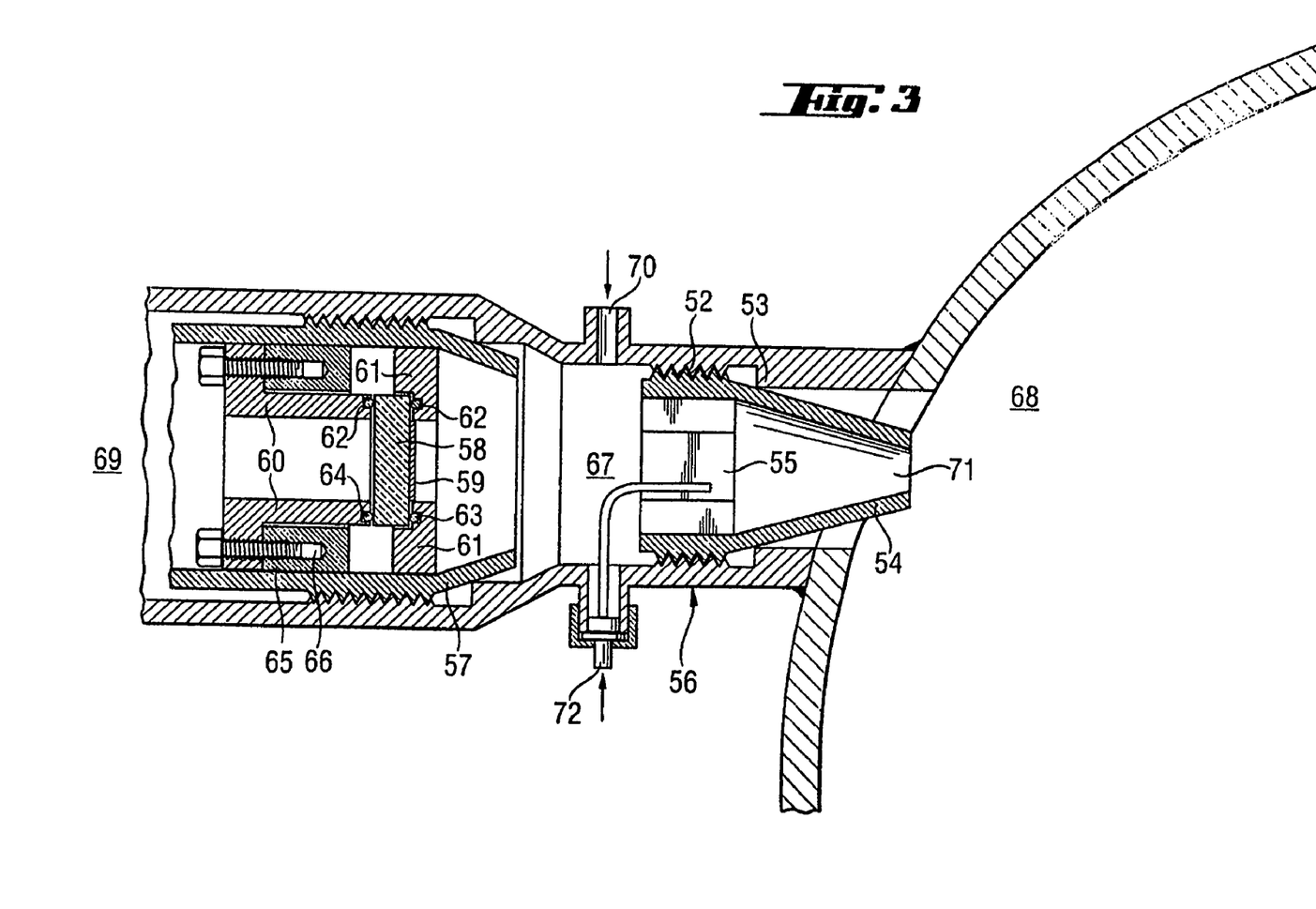
FIG. 3 shows a further modification of the device of FIG. 1 depicted in longitudinal section.

A further preferred embodiment shown in FIG. 3 resembles the variant shown in FIG. 2. However, the further gas inlet (72) in this case continues in the direction of the opening (71) and serves to introduce gaseous promoter substance. The gas inlet (70) serves only to feed in flushing gas, which is preferably an inert gas. In this way, the generation of free radicals from the promoter substance occurs in the vicinity of the reaction space (68) and away from the optical window (58). This makes further protection of the optical window (58) against carbon deposits possible.

As radiation source, it is possible to use any device whose radiation is suitable for the photolysis of components of the reaction mixture. This can be a UV lamp, (e.g. a metal vapor lamp) or a laser. When lasers are used, it is unimportant in the case of the arrangement proposed here whether a pulsed laser or a continuous laser is used. Excimer lamps can also be used as light source.

The radiation used can be injected in various ways. Thus, for example the light can be injected through a bundle of light conductors. The light source can also (e.g. when a metal vapor lamp or excimer lamp is used) be installed directly in the barrel (57) behind the optical window. In this case, appropriate cooling is preferably provided. The light can also be injected through a further window into the barrel (57) and be deflected by means of mirrors onto the window (58).

In a particular embodiment, a device analogous to those described in DE-A-198 45 512 and DE-Gbm-200 03 712 is used for the injection of light. The previously known devices are employed for observing processes in the combustion chamber of operating internal combustion engines and are, for example used in the form of spark plug adapters. Apart from their actual intended purpose, viz. the visual observation of combustion processes, such devices are, owing to their pressure resistance and heat resistance, likewise suitable for injection of light into chemical reactors in which similar pressure and temperature conditions as in running internal combustion engines prevail.

If such devices are used, the optical window depicted in FIGS. 1, 2 and 3 together with the sealing system described can be dispensed with. The light transmission line would then be screwed in the form of an adapter analogous to one or more spark plug adapters into a separating wall located in the barrel (57).

The device shown in FIG. 1 can be installed in a conventional tube reactor for carrying out free-radical gas-phase reactions.

Figure 4:
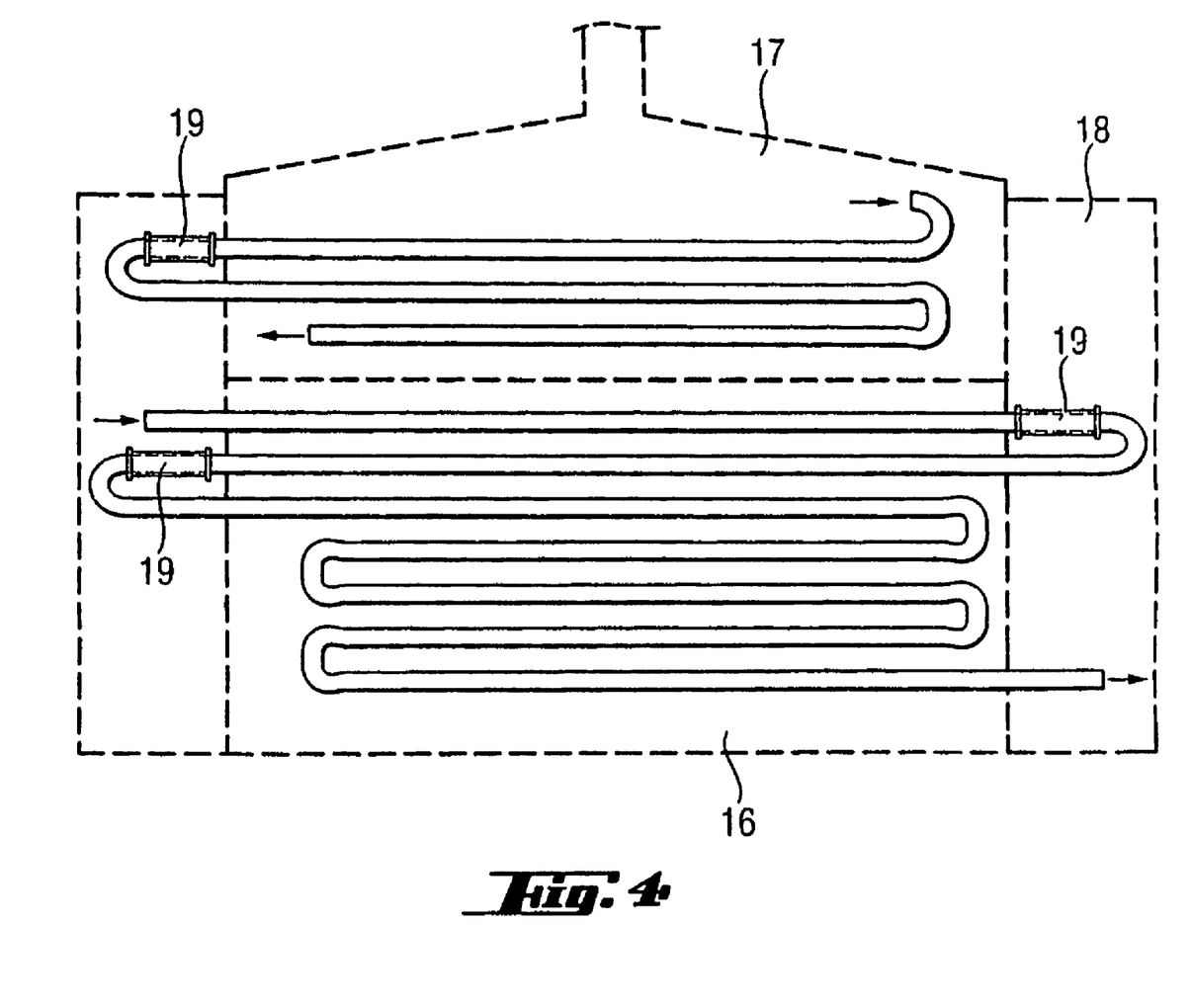
FIG. 4 shows a tube reactor with the device of FIG. 1 in longitudinal section.

A possible arrangement of the device of the invention on the reaction tube is shown in FIG. 4. A holder which has a thread and a projection (53) which forms a circumferential sealing edge is welded onto the reaction tube.

If the device described in FIG. 1 is then screwed into the holder as described above, a reliable seal is formed.

The tube reactor comprises a furnace and a reaction tube.

In general, such a furnace fired by means of a primary energy carrier, e.g. by means of oil or gas, is divided into a radiation zone (16) and a convection zone (17).

In the radiation zone (16), the heat required for the pyrolysis is transferred to the reaction tube mainly by radiation from the furnace walls heated by the burner.

In the convection zone (17), the energy content of the hot flue gases leaving the radiation zone is realized by means of convective heat transfer. The starter material for the free-radical gas-phase reaction can be preheated, vaporized or superheated in this way. The generation of steam and/or preheating of combustion air are likewise possible.

In a typical arrangement as described, for example in EP-A-264,065, liquid starting material for the free-radical gas-phase reaction is firstly preheated in the convection zone of the reactor and then vaporized in a dedicated vaporizer outside the reactor. The gaseous starting material for the free-radical gas-phase reaction is then conveyed back into the convection zone and superheated there, with the pyrolysis reaction being able to start at this point.

After it has been superheated, the starting material for the free-radical gas-phase reaction enters the radiation zone where thermal dissociation to form the product (mixture) takes place.

Due to the high temperatures prevailing in the radiation zone and at the entrance to the convection zone, it is advantageous for the device depicted in FIG. 1 not to be located directly within these zones, since otherwise, for example setting of a defined temperature of the heated gas or gas mixture which comprises free radicals and is introduced to promote the dissociation reaction is not possible or possible only with difficulty.

Preference is therefore given to an arrangement as shown schematically in FIG. 4.

Here, the reactor is extended by means of at least two additional, unheated compartments (18) which can be thermally insulated. Loops of the reaction tube are then passed from the actual radiation or convection zone (16, 17) through these compartments (18). The device for injecting electromagnetic radiation as shown in FIG. 1 (19) is then installed in these loops, preferably at the bends of the loops and opening into the straight lengths of these loops, i.e. built into the reaction tube, so that the gas stream of the reaction mixture can be treated with electromagnetic radiation at these points.

The loops of the reaction tube passed from the radiation or convection zone (16, 17) into the unheated compartments (18) are preferably provided with thermal insulation. In this case, the outer walls of the compartment do not necessarily have to have a thermal insulation function.

The invention claimed is:

1. A device for injecting electromagnetic radiation into a reactor for carrying out free-radical gas-phase reactions, which comprises the elements:
   a) a compartment which is separated from the reaction space of the reactor and is
   b) connected to the reaction space of the reactor via at least one opening,
   c) at least one feed line for introducing a flushing gas into the compartment, and also
   d) at least one source of electromagnetic radiation which is arranged so that
   e) the electromagnetic radiation passes through the compartment and the reaction space of the reactor adjoining the compartment.

2. The device as claimed in claim 1, characterized in that it has an optical window and/or another light transmission line into the compartment.

3. The device as claimed in claim 2, characterized in that the optical window and/or the transparent end of the other light transmission line is coated with an optically semitransparent layer which comprises a metal which is suitable as hydrogenation catalyst.

4. The device as claimed in claim 1, characterized in that it comprises two conical barrels (54, 57) arranged so that an intermediate space (67) which is provided with at least one gas feed line is formed between the barrels (54) and (57) so that a compartment separated from the reaction space (68) and from the outside (69) is formed and in that the barrel (57) arranged farthest away from the reactor contains an optically transparent window (58) and/or another light transmission line.

5. The device as claimed in claim 1, characterized in that irradiation devices which make irradiation of the entire compartment and of the adjoining reaction space possible are provided.

6. The device as claimed in claim 4, characterized in that the intermediate space (67) has a further gas inlet (72) which is continued into the compartment close to the surface of the optical window and/or the other light transmission line and makes it possible for the optical window and/or the other light transmission line and its environment to be flushed with inert gas or with inert gas and hydrogen.

7. The device as claimed in claim 4, characterized in that the intermediate space (67) has a further gas inlet (72) which is continued in the direction of the opening (71) and serves for the introduction of a gaseous promoter substance.

8. A reactor for carrying out free-radical gas-phase reactions, which comprises at least the following elements:
   i) a feed line for the feed gas stream opening into the reactor,
   ii) at least one device as claimed in claim 1 comprising a compartment and opening into the reactor for injecting electromagnetic radiation into the reactor,
   iii) a feed line for a flushing gas opening into the compartment of the device
   iv) a source of a flushing gas connected to the feed line,
   v) if appropriate, a heating device for heating the flushing gas in the feed line,
   vi) a heating device for heating and/or maintaining the temperature of the gas stream in the reactor, and
   vii) a discharge line for the product gas stream of the free-radical gas-phase reaction leading from the reactor.

9. The reactor as claimed in claim 8, characterized in that it has a reaction tube onto which a holder (53) which has a thread (52) and a projection and into which the device as claimed in claim 1 is screwed is welded.

10. The reactor as claimed in claim 9, characterized in that it comprises a furnace and a reaction tube running in a meandering fashion through the furnace, with the furnace having a radiation zone (16), a convection zone (17) and at least one unheated compartment (18) into which loops of the reaction tube are passed from the radiation or convection zone (16, 17) or from which the loops of the reaction tube are passed into the radiation or convection zone (16, 17), and the at least one device as claimed in claim 1 being located in at least one compartment (18) and being installed in the reaction tube so that electromagnetic radiation can be injected into the gas stream of the reaction mixture at these points.

11. The reactor as claimed in claim 8, characterized in that an adiabatic after-reactor is installed downstream thereof.

* * * * *